US00PP25259P2

(12) United States Plant Patent
Schaber

(10) Patent No.: US PP25,259 P2
(45) Date of Patent: Jan. 27, 2015

(54) GERANIUM PLANT NAMED 'OGLGER6082'

(50) Latin Name: *Pelargonium×hortorum*
Varietal Denomination: Oglger6082

(71) Applicant: Margaret Schaber, Encinitas, CA (US)

(72) Inventor: Margaret Schaber, Encinitas, CA (US)

(73) Assignee: Dümmen Group B.V., De Lier (NL)

( * ) Notice: Subject to any disclaimer, the term of this patent is extended or adjusted under 35 U.S.C. 154(b) by 94 days.

(21) Appl. No.: 13/815,477

(22) Filed: Mar. 5, 2013

(51) Int. Cl.
*A01H 5/00* (2006.01)

(52) U.S. Cl.
USPC ..... Plt./325

(58) Field of Classification Search
USPC ..... Plt./325
See application file for complete search history.

*Primary Examiner* — Annette Para
(74) *Attorney, Agent, or Firm* — C. A. Whealy

(57) ABSTRACT

A new and distinct cultivar of Zonal Geranium plant named 'Oglger6082', characterized by its upright to outwardly spreading and mounded plant habit; moderately vigorous growth habit; freely branching habit; medium green-colored leaves with distinct zonation pattern; freely flowering habit; and dark salmon pink-colored flowers arranged in large umbels held above and beyond the foliar plane on strong peduncles.

1 Drawing Sheet

Botanical designation: *Pelargonium×hortorum*.
Cultivar denomination: 'OGLGER6082'.

BACKGROUND OF THE INVENTION

The present invention relates to a new and distinct cultivar of Zonal Geranium plant, botanically known as *Pelargonium×hortorum*, and hereinafter referred to by the name 'Oglger6082'.

The new Zonal Geranium plant is a product of a planned breeding program conducted by the Inventor in Lompoc, Calif. The objective of the breeding program is to create new moderately vigorous Zonal Geranium plants with attractive leaf and flower coloration.

The new Zonal Geranium plant originated from a cross-pollination made by the Inventor in May, 2005 in Lompoc, Calif. of *Pelargonium×hortorum* 'Fisorange', disclosed in U.S. Plant Pat. No. 12,485, as the female, or seed, parent with *Pelargonium×hortorum* 'Salmon Satisfaction', disclosed in U.S. Plant Pat. No. 7,610, as the male, or pollen, parent. The new Zonal Geranium plant was discovered and selected by the Inventor as a single flowering plant from within the progeny of the stated cross-pollination in a controlled greenhouse environment in Lompoc, Calif. in May, 2006.

Asexual reproduction of the new Zonal Geranium plant by vegetative cuttings in a controlled greenhouse environment in Connellsville, Pa. has shown that the unique features of this new Zonal Geranium plant are stable and reproduced true to type in successive generations.

SUMMARY OF THE INVENTION

Plants of the new Zonal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger6082'.

These characteristics in combination distinguish 'Oglger6082' as a new and distinct Zonal Geranium plant:

1. Upright to outwardly spreading and mounded plant habit.
2. Moderately vigorous growth habit.
3. Freely branching habit.
4. Medium green-colored leaves with distinct zonation pattern.
5. Freely flowering habit.
6. Dark salmon pink-colored flowers arranged in large umbels held above and beyond the foliar plane on strong peduncles.

Plants of the new Zonal Geranium differ primarily from plants of the female parent, 'Fisorange', in plant and growth habit as plants of the new Zonal Geranium are more compact than and not as vigorous as plants of 'Fisorange'.

Plants of the new Zonal Geranium differ primarily from plants of the male parent, 'Salmon Satisfaction', in flower color as plants of 'Salmon Satisfaction' have lighter salmon pink-colored flowers.

Plants of the new Zonal Geranium can be compared to plants of *Pelargonium×hortorum* 'Evening Glow', disclosed in U.S. Plant Pat. No. 9,167. In side-by-side comparisons conducted in Encinitas, Calif., plants of the new Zonal Geranium differed primarily from plants of 'Evening Glow' in plant and growth habit as plants of the new Zonal Geranium were more compact than and not as vigorous as plants of 'Evening Glow'. In addition, plants of the new Zonal Geranium had fuller umbels than plants of 'Evening Glow'.

BRIEF DESCRIPTION OF THE PHOTOGRAPHS

The accompanying colored photographs illustrate the overall appearance of the new Zonal Geranium plant showing the colors as true as it is reasonably possible to obtain in colored reproductions of this type. Colors in the photographs may differ slightly from the color values cited in the detailed botanical description which accurately describe the colors of the new Zonal Geranium plant.

The photograph at the bottom of the sheet comprises a side perspective view of a typical flowering plant of 'Oglger6082' grown in a container.

The photograph at the top of the sheet is a close-up view of a typical flowering plant of 'Oglger6082'.

DETAILED BOTANICAL DESCRIPTION

The aforementioned photographs and following observations, measurements and values describe plants grown during the early spring in 16.5-cm containers in a polyethylene-covered greenhouse in Encinitas, Calif. and under cultural conditions which closely approximate Zonal Geranium commercial production. During the production of the plants, day temperatures averaged 27° C., night temperatures averaged 18° C. and light levels averaged 4,000 foot-candles. Plants were 17 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×hortorum* 'Oglger6082'.

Parentage:

*Female, or seed, parent.*—*Pelargonium×hortorum* 'Fisorange', disclosed in U.S. Plant Pat. No. 12,485.

*Male or pollen parent.*—*Pelargonium×hortorum* 'Salmon Satisfaction', disclosed in U.S. Plant Pat. No. 7,610.

Propagation:

*Type.*—By vegetative cuttings.

*Time to initiate roots, summer.*—About ten days at temperatures about 20° C.

*Time to initiate roots, winter.*—About two weeks at temperatures about of 16° C.

*Time to produce a rooted young plant, summer.*—About four weeks at temperatures about 20° C.

*Time to produce a rooted young plant, winter.*—About four weeks at temperatures about 16° C.

*Root description.*—Medium in thickness, fleshy; white in color.

*Rooting habit.*—Moderately freely branching; medium density.

Plant description:

*Plant and growth habit.*—Upright to outwardly spreading and mounding plant habit; moderately vigorous growth habit.

*Branching habit.*—Freely branching habit with about six primary lateral branches developing per plant, each primary lateral branch with secondary lateral branches; dense and bushy appearance; pinching enhances lateral branch development.

*Plant height, to top of umbels.*—About 34 cm.

*Plant height, to top of foliar plane.*—About 23 cm.

*Plant diameter (spread).*—About 29 cm by 35 cm.

*Lateral branches.*—Length: About 21.5 cm. Diameter: About 9 mm. Internode length: About 3.2 cm. Texture: Pubescent; minute. Strength: Strong. Color: Close to 146A.

Foliage description:

*Arrangement.*—Alternate; simple.

*Length.*—About 6.4 cm.

*Width.*—About 8 cm.

*Shape.*—Reniform.

*Apex.*—Rounded.

*Base.*—Cordate.

*Margin.*—Crenate.

*Venation pattern.*—Palmate, reticulate.

*Texture, upper and lower surfaces.*—Pubescent, minute.

*Color.*—Developing leaves, upper surface: Close to 137A. Developing leaves, lower surface: Close to 147B. Fully expanded leaves, upper surface: Close to 137B; venation, close to 137D. Zonation pattern: Location: About 8 mm from upper leaf surface margin. Width: About 1.5 cm. Color: Close to N199B. Fully expanded leaves, lower surface: Close to 147B; venation, close to 147C.

*Petiole.*—Length: About 6.7 cm. Diameter: About 2.5 mm. Texture, upper and lower surfaces: Pubescent. Color, upper and lower surfaces: Close to 146B.

Flower description:

*Flower arrangement.*—Round semi-double flowers arranged in large hemispherical to nearly spherical umbels arising from apical leaf axils; umbels displayed above and beyond the foliar plane on strong peduncles; umbels mostly upright and flowers face upright or outwardly.

*Fragrance.*—None detected.

*Quantity of flowers.*—Freely flowering habit; about 38 to 40 flowers per umbel and about ten umbels per plant at one time.

*Flowering season.*—In California, flowering is continuous during the spring and summer.

*Flower longevity.*—Individual flowers last about five to seven days on the plant; flowers persistent.

*Umbel height.*—About 8 cm.

*Umbel diameter.*—About 9.8 cm.

*Flower diameter.*—About 4.3 cm.

*Flower depth (height).*—About 2.3 cm.

*Flower buds.*—Length: About 1.7 cm. Diameter: About 1 cm. Shape: Oval. Color: Close to 55C to 55D.

*Petals.*—Quantity per flower and arrangement: Typically eight to nine in about two whorls. Length: About 2.4 cm. Width: About 2 cm. Shape: Obovate. Apex: Rounded. Base: Acute. Margin: Entire. Texture, upper and lower surfaces: Smooth, glabrous; velvety. Color: When opening, upper surface: Close to 43C. When opening, lower surface: Close to 43D. Fully opened, upper surface: Close to 48B to 48C; venation, close to 48B to 48C; color becoming closer to 49A with development. Fully opened, lower surface: Close to 54C to 54D; venation, close to 54C to 54D; color becoming closer to 55C to 55D with development.

*Petaloids.*—Quantity per flower and arrangement: Typically two or three central to the whorls of petals. Length: Variable, about 1.2 cm. Width: Variable, about 4 mm. Shape: Variable, somewhat distorted, roughly lanceolate. Apex: Rounded. Base: Acute. Margin: Entire, curled. Texture, upper and lower surfaces: Smooth, glabrous; velvety. Color: When opening, upper surface: Close to 47C. When opening, lower surface: Close to 47D. Fully opened, upper surface: Close to 47D. Fully opened, lower surface: Close to 48C.

*Sepals.*—Quantity per flower: Typically five, occasionally six, arranged in a single whorl. Length: About 1 cm. Width: About 3 mm. Shape: Narrowly elliptical. Apex: Acuminate. Base: Truncate. Margin: Entire. Texture, upper surface: Smooth, glabrous. Texture, lower surface: Pubescent. Color, upper surface: Close to 146D. Color, lower surface: Close to 146C.

*Peduncle* (*umbel stem*).—Length: About 17 cm. Diameter: About 3.5 mm. Angle: About 35° to 45° from stem axis. Strength: Strong. Texture: Pubescent; minute. Color: Close to 146C.

*Pedicel* (*individual flower stem*).—Length: About 2.3 cm. Diameter: About 1.5 mm. Angle: About 15° to 55° from peduncle axis. Strength: Strong. Texture: Pubescent; minute. Color: Close to 146D tinted with close to 183B to 183C.

*Reproductive organs*.—Androecium: Stamen quantity per flower: About five to seven; occasionally modified into petaloids. Filament length: About 8 mm. Filament color: Close to NN155D. Anther length: About 2.5 mm. Anther shape: Oblong. Anther color: Close to 51B. Pollen amount: Scarce. Pollen color: Close to 178C. Gynoecium: Pistil quantity per flower: One. Pistil length: About 9 mm. Stigma shape: Five-parted, star-shaped; recurved. Stigma color: Close to 60B. Style length: About 2.5 mm. Style color: Close to 60D. Ovary color: Close to 148C.

*Seeds and fruits*.—Seed and fruit development have not been observed on plants of the new Zonal Geranium.

Disease & pest resistance: Plants of the new Zonal Geranium have not been observed to be resistant to pathogens and pests common to Zonal Geranium plants.

Temperature tolerance: Plants of the new Zonal Geranium have been observed to tolerate temperatures ranging from about 1° C. to about 35° C.

It is claimed:

1. A new and distinct Zonal Geranium plant named 'Oglger6082' as illustrated and described.

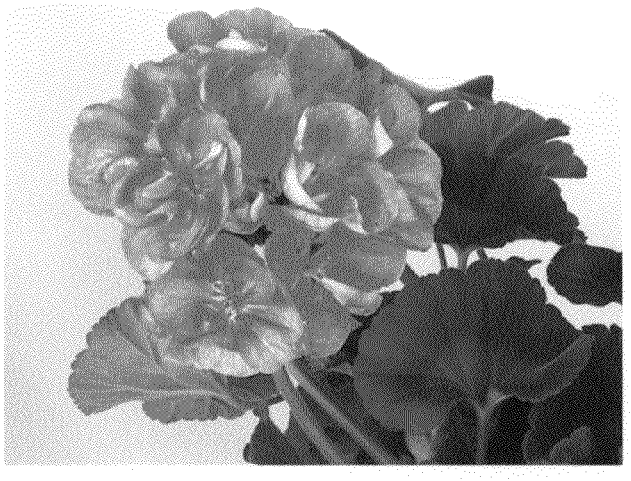
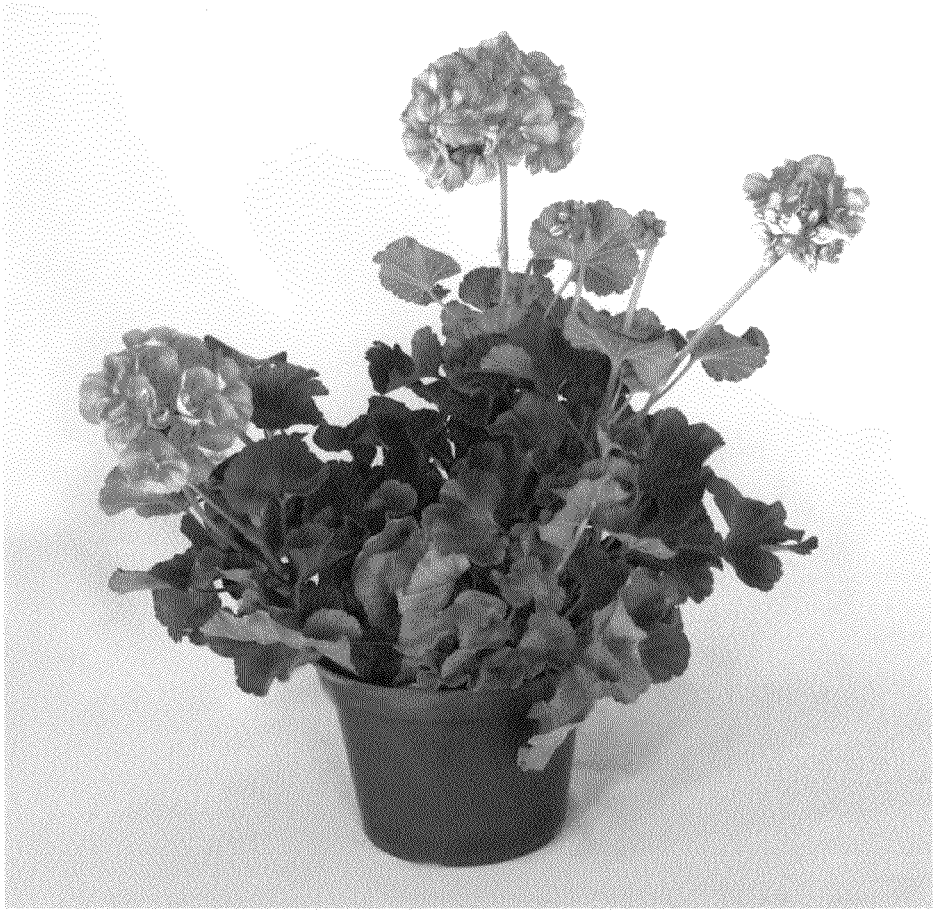

* * * * *